United States Patent [19]

Marks et al.

[11] Patent Number: 5,480,952
[45] Date of Patent: Jan. 2, 1996

[54] ZIRCONIUM AND HAFNIUM-CATALYZED POLYMERIZATION OF METHYLENECYCLOPROPANE

[75] Inventors: Tobin J. Marks, Evanston, Ill.; Xinmin Yang, Somerset, N.J.; Li Jia, Evanston, Ill.

[73] Assignee: Northwestern University, Evanston, Ill.

[21] Appl. No.: 399,390

[22] Filed: Mar. 6, 1995

[51] Int. Cl.⁶ .................................................. C08F 32/02
[52] U.S. Cl. .................... 526/308; 526/134; 526/160; 526/170; 526/348; 526/126
[58] Field of Search ................................. 526/308, 134, 526/126

[56] References Cited

U.S. PATENT DOCUMENTS

| | | | |
|---|---|---|---|
| 5,300,598 | 4/1994 | Marks et al. | 526/134 |
| 5,395,906 | 3/1995 | Marks et al. | 526/308 |
| 5,422,406 | 6/1995 | Yang | 526/126 |

OTHER PUBLICATIONS

Takemoto, K. et al., *Vinylpolymerisation*, Die Makromolekulare Chemie, 109, pp. 81–86, 1967.
Koster, R.; Arora, S. and Binger, P., Angew Chem. Int. Edit., 8, 205–206, 1969.
Pinazzi, P. et al., *Polymerization of Methylenecylobutane, Synthesis of an Isopolyisoprene*, Die Makromolekulare Chemie, 122, pp. 105–122, 1969.
Pinazzi, P. et al., *Polymerisation du Methylenecyclobutane Obtention de L'Isocaoutchouc*, Die Makromolekulare Chemie, 147, pp. 15–33, 1971.
Pinazzi, P. et al., *L'Isocautchone, Etude des parametres de cyclisation et d–Isomerisation*, Die Makromolekulare Chime, 148, pp. 81–92, 1971.
Rossi, R. et al., *On the Ring Opening Polymerization of Methylenecyclobutane*, Macromolecules, 5(3), pp. 247–249, 1972.
Watson, P. L., Roe, C., J. Am. Chem. Soc., 104, 6471–6473, 1982.
Watson, P. L., J. Chem. Soc. Chem. Commu., 276–277, 1983.
Jeske, G.; Lauke, H.; Mauermann, H.; Sweptson, P. N.; Schmann, H.; Marks, T. J., J. Am. Chem. Soc., 107, 8091–8103, 1985.
Hiraguri, Y. et al., *Radical Polymerization of 3–Substituted–1–Methylenecyclobutanes*, Journal of Polymer Science: Part C: Polymer Letters, vol. 26, pp. 381–384, 1988.
Jordan, R. F., Adv. Organomet Chem., 32, 325–387, 1991.
Yang, X.; Stern, C. L. and Marks, T. J., Am. Chem. Soc., 113, pp. 3623–3625, 1991.
Trost, B. M.; Shi, Y., J. Am. Chem. Soc., 115, pp. 9420–9438, 1993.
Yang, X.; Jia, L. and Marks, T. J., J. Am. Chem. Soc., 115, 3392–3393, 1993.
Yang, X.; Seyam, A. M. amd Marks, T. J., Macromolecules, 27, 4625–4626, 1994.

*Primary Examiner*—Fred Zitomer
*Attorney, Agent, or Firm*—Welsh & Katz, Ltd.

[57] ABSTRACT

A polymer having a repeating unit of

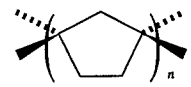

and
a method for preparing it through Zr-catalyzed polymerization of methylenecyclopropane is disclosed.

1 Claim, 1 Drawing Sheet

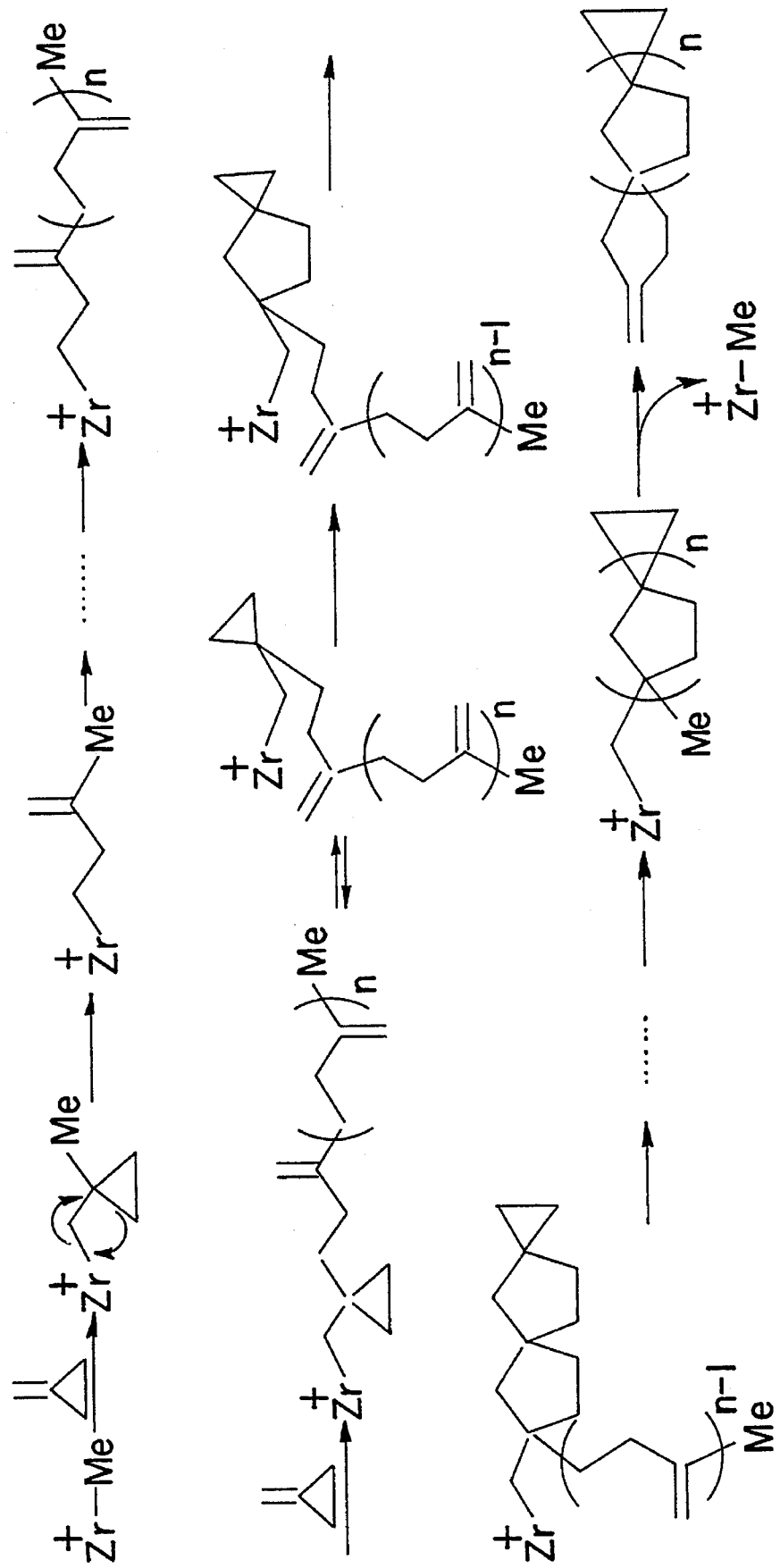

ZIRCONIUM AND HAFNIUM-CATALYZED POLYMERIZATION OF METHYLENECYCLOPROPANE

The United States Government has rights in this invention pursuant to DOE Grant No. DE-FG02-86ER13511. This is a continuation-in-part of application Ser. No. 136,217, Filed Oct. 4, 1993, which is a continuation-in-part of U.S. Pat. No. 5,300,598.

BACKGROUND OF THE INVENTION

This application relates to catalysts and more particularly to homogeneous catalysts for use in polymerization via the ring opening of strained ring systems, and the polymers formed with such catalysts.

As discussed in U.S. Pat No. 5,300,598, in the presence of ring-opening Ziegler catalysts, methylenecyclobutane can be polymerized into a polymer consisting of the structure A, through a ring-opening mechanism.

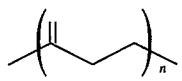

A

Polymers having rigid backbones often possess unique properties including high modulus and strength, chirality, and liquid crystallinity which properties lend themselves to use as a structural components or thermoplastic elastomers in structural applications such as fibers, aircraft and automotive parts or in optical devices, such as liquid crystal displays and others. Examples are polyisocyanides, polycarbodiimides, polybenzimidazoles, polyacetylenes, polyimides, and polyamides. The structural stiffness of these polymers is frequently achieved through delocalized $\pi$ bonding and secondary chemical interactions such as hydrogen bonding. Linear rigid macromolecules consisting solely of saturated hydrocarbon backbones, the rigidity of which derives from $\sigma$ bond linkages, are virtually unknown, and would represent a new class of isomeric polyolefins. One apparent reason for the paucity lies in the lack of efficient synthetic approaches, since their logical monomeric precursors would necessarily be olefins, which have limited polymerization pathways. However, electrophilic $d^0$ metallocene centers appear to be highly efficient in a number of carbon-carbon bond transformations.

SUMMARY OF THE INVENTION

Therefore, an object of the subject invention is a novel catalyst to produce polymers having a rigid backbone.

A further object of the subject invention is a polymer formed from a catalytic olefin polymerization process which operates via a ring-opening mechanism.

A still further object of the subject invention is a polymer formed through the use of a catalyst by which electrophilic metallocene cations catalyze the facile regioselective ring-opening homopolymerization of methylenecyclopropane type monomers using well-defined homogeneous Zr, Ti, and Hf catalysts.

A further object of the subject invention is a polymer of the structure:

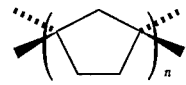

B which may be depicted as:

C or

D

These and other objects of the subject inventions attained by a method involving the sequential ring-opening-zipping-up Ziegler polymerization of methylenecyclopropane catalyzed by $(Me_5Cp)_2MMe^+MeB(C_6F_5)_4^-$, (M=Ti, Zr, Hf) and the characterization of the resulting rigid-rod/helix polymer of structure B, including the structure A above.

In the alternate nomenclature of the American Chemical Society, land focusing on the smallest structural repeating unit, the polymer of the subject invention can be named poly(1,4:2,2-butanatetrayl), and thus is represented by the structure

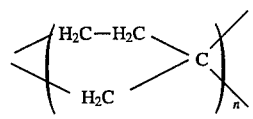

E n = 15–1000 polymerization of methylenecyclopropane proceeds rapidly in a dilute toluene solutions of $(Me_5Cp)_2MMe^+$ $MeB(C_6F_5)_4^-$, M=Zr, Hf) under rigorously anhydrous/anaerobic conditions, even at temperatures as low as –30° C., to result in the polymer poly(1,4:2,2-butanatetrayl) having a typical molecular weight of 1,000–39,000. The resulting polymers are isolated after toluene removal followed by washing.

BRIEF DESCRIPTION OF THE DRAWING

The FIGURE is a schematic of the reaction sequence for preparing the polymers of the subject invention.

DETAILED DESCRIPTION OF THE INVENTION

Facile $\beta$-alkyl transpositions are a distinctive feature of electrophilic $d^0f^n$ hydrocarbyl chemistry (e.g., equation (I)) and

I represent an important chain transfer channel in certain olefin polymerization processes. In principle, such transpositions might also provide an unusual pathway to functionalized polyolefins by coupling olefin insertion and strained monomer ring-opening sequences (equation (II)).

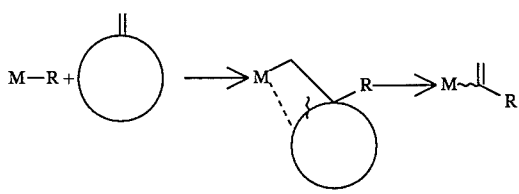

II

In the presence of conventional heterogeneous Ziegler-Natta catalysts, methylenecyclopropane undergoes a sluggish reaction to afford polymers having ring-opening or mixed ring-opening/insertion-derived microstructures. The ring-opened structures were ascribed to oxidative addition at the C3–C4 junctures of A. As stated above, the subject invention involves electrophilic zirconocene or hafnocene cations, which catalyze the facile, regioselective ring-opening homopolymerization of exo-methylene cyclic organic compounds via a β-alkyl shift mechanism.

The exo-methylene cyclic organic compounds which may be used in the subject invention generally may be represented by the formula:
where R', R", and R"' are organic fragments which may include O, N, S or P. Preferably, the monomer is methylenecyclopropane In general, reaction of the catalyst $L_1L_2MR^+X^-$ or $(LR'_2SiNR")MR^+X^-$, where L is a cyclopentadienyl-containing ligand, M=Zr or Hf, and R, R" is an alkyl (C=1–5), hydride, or aryl (C=5–20), $X^-$ is a non-coordinating charge-compensating anion derived from $B(C_6F_5)_3$, $B(C_6F_5)_4$, or methylalumoxane or $(L_2LnH)_2$ (Ln=a lanthanide element) with methylenecyclopropane or a substituted methylenecyclopropane proceeds rapidly in toluene solution to yield, after work-up, a polymer with a structure such as B. Examples of viable catalysts are $(C_5Me_5)_2ZrMe^+MeB(C_6F_5)_3^-$ and $[(C_5Me_4(SiMe_2)NtBu]ZrMe^+MeB(C_6F_5)_3^-$, or $(C_5H_5)_2ZrR_2$ and methylalumoxane, (R=alkly, aryl hydride, halide or alkoxide C=1–102). Other nonpolar solvents, both aliphatic (C=1–12) and aromatic (C=6–20) as well as others may be used. $^1H$ and $^{13}C$ NMR spectra reveal that the polymer microstructure which results is dependent on the ancillary ligands at the metal center with $L^1=L^2=72^5-Me_5C_5$ and $L^1$, $L^2=Me_4C_5(SiMe_2)N^tBu$ giving highest selectivity. The length of reaction time/extent of conversion appears to have no detectable effect on selectively.

EXAMPLES

All operations were performed with rigorous exclusion of oxygen and moisture in flamed Schlenk-type glassware in a dual manifold Schlenk line or interfaced to a high vacuum ($10^{-5}$ torr) system, or in a nitrogen or argon filled glovebox with a high capacity atmosphere recirculator. Argon, ethylene and propylene were purified by passage through a supported MnO oxygen removal column and a molecular sieve column. Aliphatic hydrocarbon solvents were pretreated with concentrated $H_2SO_4$, $KMnO_4$ solution, $MgSO_4$ and Na, 4 Å molecular sieves. All reaction solvents were distilled from Na/K/benzophenone under nitrogen and were condensed and stored in vacuo on the vacuum line containing a small amount of $[Ti(\eta^5-C_5H_5)_2Cl]_2$ as indicator. Methylenecyclopropane was additionally dried over Na/K.

EXAMPLES preparation of Catalyst

Synthesis of $(C_5Me_5)_2ZrMe+MeB(C_6F_5)_3-$ $(C_5Me_5)_2ZrMe_2$ (0.148 g, 0.379 mmol) and $B(C_6F_5)_3$ (0.194 g, 0.379 mmol) are loaded into a 25 mL flask. Benzene (10 mL) was then vacuum transferred into this flask at −78° C. As the mixture is slowly warmed to ambient temperature. A clear solution is first seen but it quickly becomes cloudy as solids begin to precipitate. After stirring for 2.5 h, the mixture is filtered. The light yellow solid is washed once with a small amount of benzene and dried under vacuum. Yield, 65%.

Synthesis of $[C_5Me_4(SiMe_2)N^tBu]ZrCH_3+CH_3B(C_6F_5)_3-$ $C_5Me_{4\ 1\ (SiMe2)}N^tBu$(0.148 g, 0.400 mmol) and $B(C_6F_5)_3$ (0.205 g, 0.400 tool) are loaded into a 25 mL flask in the glovebox. Benzene (15 mL) is then vacuum-transferred into this flask at −78° C. The mixture is slowly warmed to room temperature and stirred for 1.5 h. At this time, large quantities of solid precipitate. Pentane (10 mL) is vacuum-transferred into the flask and the mixture is filtered after stirring. The light yellow solid is washed once with 5 mL of pentane and dried under vacuum. Yield, 72%.

EXAMPLE 1

Homo-polymerization of Methylenecyclopropane.

$(C_5Me_5)_2ZrMe^+MeB(C_6F_5)_3-$(6 mg) is loaded into a 25 mL flask in a glovebox. Toluene (10 mL) and methylenecyclopropane (0.1 mL) are vacuum-transferred into the above flask at −78° C. The flask is backfilled with Ar and the solution stirred at room temperature for 16 h. After removing the volatiles under vacuum, the polymeric product is washed several times with toluene and dried under vacuum. Yield, about 90%. The polymer is characterized by $^1H$, and $^{13}C$ NMR spectroscopy. $^1H$(tol-$d_8$,RT) δ1.6 ppm; $^{13}C$(tol-$d_8$, 105° C.) δ41.32(t,$^1J_{C-H}$=126.3 Hz) ppm, 50.11(s), 56.66(t, $^1J_{C-H}$=128.2 Hz).

EXAMPLE 2 polymerization of Methylenecyclopropane by $[C_5Me_4(SiMe_2)N^tBu]ZrMe^+MeB(C_6F_5)_3-$.

$C_5Me_4(SiMe_2)N^tBuZrMe^+MeB(C_6F_5)_3-$(19.5 mg) is loaded into a 25 ml flask in a glovebox. Toluene (10 ml) and methylenecyclopropane (1.0 ml) are vacuum-transferred into the flask at −78° C. The solution is stirred at room temperature for 1 hour. The solution turns into a solid phase. The white solid polymeric product is collected by washing with ethanol and dried under vacuum.

The resulting polymers have been characterized by a combination of several NMR techniques at high temperature. Both $^1H$ and $^{13}C$ spectra indicate that the polymer chains have saturated hydrocarbon backbones. DEPT $^{13}C$ experiments show that the three major resonances at δ55, 51 and 42 ppm are secondary, quaternary, and secondary carbon atoms, respectively. The intensity of these three signals has a ratio of 1:2:2. Two-dimensional HETCOR experiments reveal that the major components of the proton spectrum (δ6 1.5–1.7ppm) are attached to the carbons at δ55 or 42 ppm. The pattern of the linkage between the carbon atoms is then determined to be $C_{55ppm}-C_{51ppm}-C_{42ppm}$ by two-dimensional $^{13}C$ NMR. The only chain structure compatible with the above observations is structure B. The structure of the chain is also supported by formation of the same polymer in the reaction of polymer A in concentrated toluene solutions of $(Me_5Cp)_2ZrMe^+MeB(C_6F_5)^{-5}$ at room temperature. The unopened cyclopropyl structures (a signal at δ 6 0.5 ppm in $^1H$ spectrum and those at δ6 14 ppm in $^{13}C$. spectrum) observed are assigned to end groups of the polymer based on the absence of significant quantities of the unzipped precursor structure A. The terminal olefinic structure (signals at δ 5.1 ppm, and 2.2 ppm of the allylic proton) can be assigned to either structure A or end groups which are the result of β-methyl elimination, apparently polymers produced at lower temperatures.

The formation of polymeric structure B can be rationalized by a ring-opening-zipping-up mechanism (The FIG.). The reaction must begin with the ring-opening polymerization of methylenecyclopropane. Then at a certain step, competing intramolecular C=C bond insertion is initiated, and the zipping-up process starts. That the isomerization of A to B requires high catalyst concentrations and prolonged reaction time argues against the extensive participation of intermolecular mechanisms which involve first the elimination of the polymer A from the catalytic center, and then reinsertion of vinylic end groups of the polymer A followed by sequential zipping-up reactions. Although the initiation of the zipping-up process can follow several possible routes, observation of the cyclopropyl structures as end groups suggests that the zipping-up reactions start mainly at the point when one molecule of methylenecyclopropane inserts, then instead of β-alkyl shift ring-opening, competing intramolecular insertion of a C=C bond occurs leading to sequential intramolecular insertion along the entire polymer chain.

TABLE I

| | Polymerization of Methylenecyclopropane Using $(Me_5Cp)_2ZrMe^+MeB(C_6F_5)_3^-$ as Catalyst. | | | | | |
|---|---|---|---|---|---|---|
| Entry | Catalyst Amount (mg) | Methylene-cyclopropane (mg) | Reaction Temperature (°C.) | Reaction Time (h) | Yield of Polymer (mg) | $M_w(M_n)^d$ (x 1000) |
| 1[a] | 6.5 | 398 | −30 | 2.5 | 340 | 7,100(1,200) |
| 2[b] | 5.0 | 70 | 0 | 4.0 | 50 | 29,700(11,300) |
| 3[a,c] | 10.2 | 230 | 25 | | 160 | 39,200(13,900) |

[a]Toluene (15 mL) as solvent
[b]Reaction in NMR tube, toluene –$d^8$ as solvent
[c]Dihydrogen was used to re-initiate the reaction at 20 min intervals. The total reaction time was 4 hours.
[d]GPC vs polystyrene The regioselectivity of polymerization decreases at high temperature, and the composition having structure A increases. Fractions soluble in a mixture of toluene/ethanol (2:1 in volume) are enriched in structure A. Interestingly, polymerization pauses at room temperature before methylenecyclopropane is completely consumed. The loss of activity is not due to poisoning of the catalyst since dihydrogen can re-activate the polymerization. Thus, chain length is completely controllable from as little as n-10 to n=100,000 or more, dependent on the supply of methylenecyclopropane.

Since the $^{13}C$ NMR spectrum only shows three major resonances it would appear that the polymerization is stereoselective, in other words the polymer is either a rod-like polymer as in FIG. I or a helix-like polymer as in FIG. II. The control over stereochemistry during zipping up must be related to the relative conformation of the adjacent ring that formed in the preceding step before since 2 is an achiral compound.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A polymer having the structure:

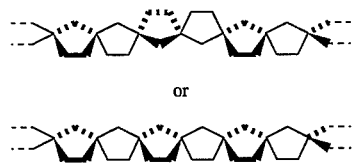

Poly (1,4,2: 2-butanatetrayl) or the repeating unit of:

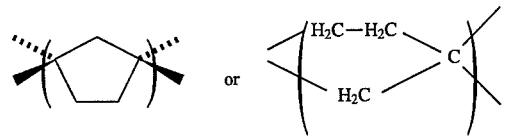

* * * * *